(12) United States Patent
Chao et al.

(10) Patent No.: US 11,395,869 B2
(45) Date of Patent: Jul. 26, 2022

(54) ARTERIAL CANNULA WHICH ALLOWS PERFUSION ALONG OPPOSING DIRECTIONS WITHIN A CANNULATED VESSEL

(71) Applicants: Tar Toong Victor Chao, Singapore (SG); Chong Hee Lim, Singapore (SG)

(72) Inventors: Tar Toong Victor Chao, Singapore (SG); Chong Hee Lim, Singapore (SG)

( * ) Notice: Subject to any disclaimer, the term of this patent is extended or adjusted under 35 U.S.C. 154(b) by 285 days.

(21) Appl. No.: 16/575,325

(22) Filed: Sep. 18, 2019

(65) Prior Publication Data

US 2020/0114062 A1    Apr. 16, 2020

Related U.S. Application Data

(63) Continuation of application No. 14/419,431, filed on Feb. 3, 2015, now Pat. No. 10,456,518.

(51) Int. Cl.
*A61M 1/36* (2006.01)
*A61M 25/00* (2006.01)
*A61M 25/04* (2006.01)

(52) U.S. Cl.
CPC ...... *A61M 1/3659* (2014.02); *A61M 25/0029* (2013.01); *A61M 25/0043* (2013.01); *A61M 25/04* (2013.01); *A61M 25/0052* (2013.01); *A61M 25/0054* (2013.01); *A61M 2025/0008* (2013.01)

(58) Field of Classification Search
CPC .......... A61M 25/0693; A61M 25/0662; A61M 25/007; A61M 25/1002; A61M 25/0029; A61M 25/0043; A61M 25/0054; A61M 2025/0008; A61M 2025/0079; A61M 2025/0246; A61M 1/3667; A61M 1/3666; A61M 1/3659; A61M 1/3638; A61M 1/3653

See application file for complete search history.

(56) References Cited

U.S. PATENT DOCUMENTS

| 2007/0049871 A1* | 3/2007 | Fleischer | .............. | A61M 25/02 |
| | | | | 604/180 |
| 2008/0033570 A1* | 2/2008 | Blitz | ....................... | A61F 2/958 |
| | | | | 623/23.7 |

\* cited by examiner

*Primary Examiner* — Nathan R Price
*Assistant Examiner* — Justin L Zamory

(57) ABSTRACT

A cannula includes at least one opening at a distal tip, and further includes multiple fenestrations that are maintainable in position substantially immediately or slightly beyond a site or point of cannula entry into a vessel. The fenestrations, in combination with the opening(s) at the cannula's distal tip, enable the simultaneous perfusion of blood into the cannulated vessel along multiple directions, including opposing or anti-parallel blood flow directions relative to a central axis of the cannulated vessel. During a medical procedure (e.g., an extra-corporeal membrane oxygenation (ECMO) procedure) blood introduced into a vessel such as the femoral artery by way of the cannula can thus exit the cannula in a manner that provides concurrent blood flow in a first direction towards the heart and a second direction away from the heart.

9 Claims, 5 Drawing Sheets

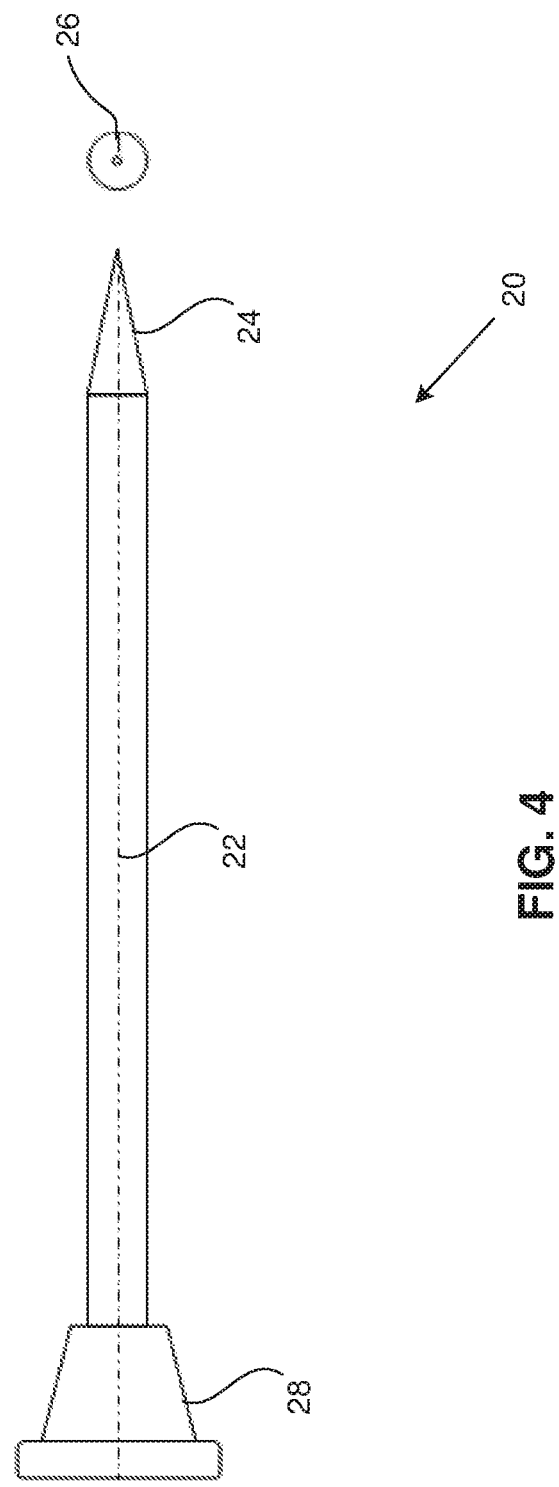

ARTERIAL CANNULA WHICH ALLOWS PERFUSION ALONG OPPOSING DIRECTIONS WITHIN A CANNULATED VESSEL

CROSS REFERENCE TO RELATED APPLICATIONS

This application is a Continuation of U.S. patent application Ser. No. 14/419,431, which is incorporated herein by reference in its entirety.

TECHNICAL FIELD

Aspects of the present disclosure are directed to a cannula having at least one opening at a distal tip, and which further includes multiple fenestrations that are maintainable in position substantially immediately or slightly beyond a site or point of cannula entry into a vessel. The fenestrations, in combination with the opening(s) at the cannula's distal tip, facilitate or enable the simultaneous perfusion of blood into the cannulated vessel along multiple directions, including opposing or anti-parallel blood flow directions relative to a central axis of the cannulated vessel. Blood introduced into a vessel such as the femoral artery by way of the cannula can thus exit the cannula in a manner that provides concurrent blood flow in a first direction towards the heart and a second direction away from the heart.

BACKGROUND

Patients with cardiopulmonary failure can be treated with mechanical circulatory support, such as veno-arterial extracorporeal membrane oxygenation (VA ECMO). In association with VA ECMO, a cannula having a proximal end and a distal tip is placed in an artery, which is commonly the femoral artery, to infuse oxygenated blood into the body. The cannula can be inserted into the artery by way of open surgical or percutaneous puncture, such as through the Seldinger technique. Blood that is directed into the cannula's proximal end exits the cannula at its distal tip, and is directed up the aorta towards the heart.

In order to supply an adequate amount of blood, the cannula needs to be sufficiently large in diameter. As a result, the cannula itself obstructs blood flow into the extremity or limb that is cannulated, which is commonly a leg. For patients on long-term support, the potential for ischemia to the cannulated limb arises due to this obstruction of blood flow. Attempts to solve this ischemia problem include the insertion of a second arterial cannula into the artery, limb-wise distal to the site of cannulation and directed downwards. This second cannula is taken off of the cardiopulmonary circuit by a Y connector and a tube. Unfortunately, this requires a second cannulation in an often sick and anticoagulated patient.

A need exists for an arterial cannula that provides adequate blood flow into the body, but which also enables blood flow into the cannulated body extremity.

SUMMARY

In accordance with an aspect of the present disclosure, a process or method of cannulating an anatomical vessel of a patient through a vessel entry point and introducing concurrent flows of oxygenated blood into the anatomical vessel in opposing flow directions during a veno-arterial extra-corporeal membrane oxygenation (VA ECMO) procedure or a cardiopulmonary bypass procedure includes:

(a) providing a cannula structure formed as an elongate tubular structure and having a length, the cannula structure including:
   a proximal opening configured to reside outside of the patient's body and by which oxygenated blood is introducible into the cannula structure for delivery into the anatomical vessel during the VA ECMO procedure or cardiopulmonary bypass procedure;
   a plurality of fluid outputs, each of the plurality of fluid outputs fluidically coupled along the length of the cannula structure to the proximal opening of the cannula structure, the plurality of fluid outputs including:
      a distal opening configured for outputting into the anatomical vessel a first portion of said oxygenated blood in a first flow direction; and
      a set of fenestrations that is distinct and spaced proximally away from the distal opening, the set of fenestrations configured for outputting into the vessel a second portion of said oxygenated blood in a second flow direction counter to the first flow direction, simultaneous with the distal opening outputting the first portion of said oxygenated blood in the first flow direction;
   a first tube disposed distal to the cannula structure's proximal opening, the first tube having an elongate length along which a plurality of fluidically coupled lumens extend therethrough, the first tube including:
      a first segment configured to entirely reside within the anatomical vessel during the VA ECMO procedure or cardiopulmonary bypass procedure, the first segment including:
         a first lumen having a proximal fluid input fluidically coupled to the proximal opening of the cannula structure and which is configured for receiving said oxygenated blood during the VA ECMO procedure or cardiopulmonary bypass procedure;
         an elongate projecting portion through which the first lumen extends; and
         the cannula structure's plurality of fluid outputs,
            wherein the distal opening resides near or at a distal end of the first tube,
            wherein the elongate projecting portion extends between the distal opening and the set of fenestrations,
            wherein the set of fenestrations resides on a section of the first segment that is (a) proximal to the elongate projecting portion, (b) configured to remain angulated within the vessel during the VA ECMO procedure or cardiopulmonary bypass procedure, and (c) disposed substantially beneath the vessel entry point such that the set of fenestrations outputs the second portion of said oxygenated blood substantially beneath the vessel entry point during the VA ECMO procedure or cardiopulmonary bypass procedure;
      a second segment proximal to the first segment and configured to essentially entirely reside external to the vessel during the VA ECMO procedure or cardiopulmonary bypass procedure, which includes a second lumen aligned with the first lumen of the first segment, and which between the cannula structure's proximal opening and distal opening is fluidically coupled to each of the cannula structure's proximal opening, the proximal fluid input of the first segment, the first lumen of the first segment, and the cannula structure's plurality of fluid outputs, and which is configured for receiving said oxygenated blood from the cannula structure's proximal opening and delivering said oxygenated blood into the proximal fluid input of the first segment during the VA ECMO procedure or cardiopulmonary bypass procedure; and an expandable or inflatable cuff which prior to and after expansion or inflation is disposed distal to the second segment and around the first segment at a first segment location slightly proximal to the set of fenestrations, wherein the expandable or inflatable cuff when expanded or inflated has a cross sectional area that is larger than each of a cross sectional area of the vessel entry point and the first segment at the location around the first segment at which the expandable or inflatable cuff is disposed, and wherein the expandable or inflatable cuff includes:
   a sleeve configured for expansion away from or contraction toward the first lumen; and
   an activation member coupled to the sleeve and configured for selectively expanding or contracting the sleeve,
   wherein the expandable or inflatable cuff when expanded or inflated is configured to reside entirely within the vessel in a position substantially beneath and immediate to the vessel entry point adjacent to the superficial wall of the vessel, proximal to the set of fenestrations relative to the length of the first tube when the vessel is cannulated and the first tube is in a correct position within the vessel during the VA ECMO procedure or cardiopulmonary bypass procedure;

(b) introducing the distal end of the first tube into the anatomical vessel through the vessel entry point;

(c) after (b), advancing portions of the first tube into the anatomical vessel until the first segment including the set of fenestrations resides within the anatomical vessel;

(d) after (c), further advancing the first tube into the anatomical vessel, such that the first segment including the set of fenestrations, the expandable or inflatable cuff, and portions of the second segment reside within the anatomical vessel;

(e) after (d), expanding or inflating the expandable or inflatable cuff;

(f) after (e), withdrawing portions of the cannula structure from the anatomical vessel until resistance is felt, indicating the expandable or inflatable cuff has contacted the superficial wall of the anatomical vessel; and (g) after (f), anchoring portions of the cannula structure to the patient's skin.

The process or method can further include, after (g):
supplying said oxygenated blood to the cannula structure's proximal opening; and
discharging the first portion of said oxygenated blood out of the distal opening in the first flow direction simultaneous with discharging the second portion of said oxygenated blood into the anatomical vessel out of the set of fenestrations in the second flow direction.

In association with the process or method, a vector flow component along a central axis of the anatomical vessel corresponding to blood output by at least some fenestrations within the set of fenestrations is antiparallel to a vector flow component along the central axis of the anatomical vessel corresponding to blood output by the distal opening.

In association with the process or method, the distal opening provides systemic blood flow to the patient's body, while the set of fenestrations provides blood flow to a limb of the patient's body during the VA ECMO or cardiopulmonary bypass procedure.

In accordance with a further aspect of the present disclosure, supplying said oxygenated blood to the cannula structure's proximal opening includes includes the proximal end of the cannula structure to a pump circuit.

In accordance with a further aspect of the present disclosure, the first segment carries a blood indicator port that is fluidically coupled to a blood indicator interface corresponding to a hub structure associated with the cannula structure, and wherein (c) of the method includes: after (b), advancing the first tube into the anatomical vessel until the blood indicator interface indicates that the set of fenestrations resides within the anatomical vessel.

In accordance with a further aspect of the present disclosure, the activation element is fluidically coupled to an activation port carried by the expandable or inflatable cuff, and wherein (e) includes: after (d), expanding or inflating the expandable or inflatable cuff by way of communication of a fluid into the activation port.

BRIEF DESCRIPTION OF THE DRAWINGS

FIG. 4 is a schematic illustration of a second tube 20 provided by a cannula assembly or structure in accordance with an embodiment of the present disclosure.

DETAILED DESCRIPTION

Figure 1:
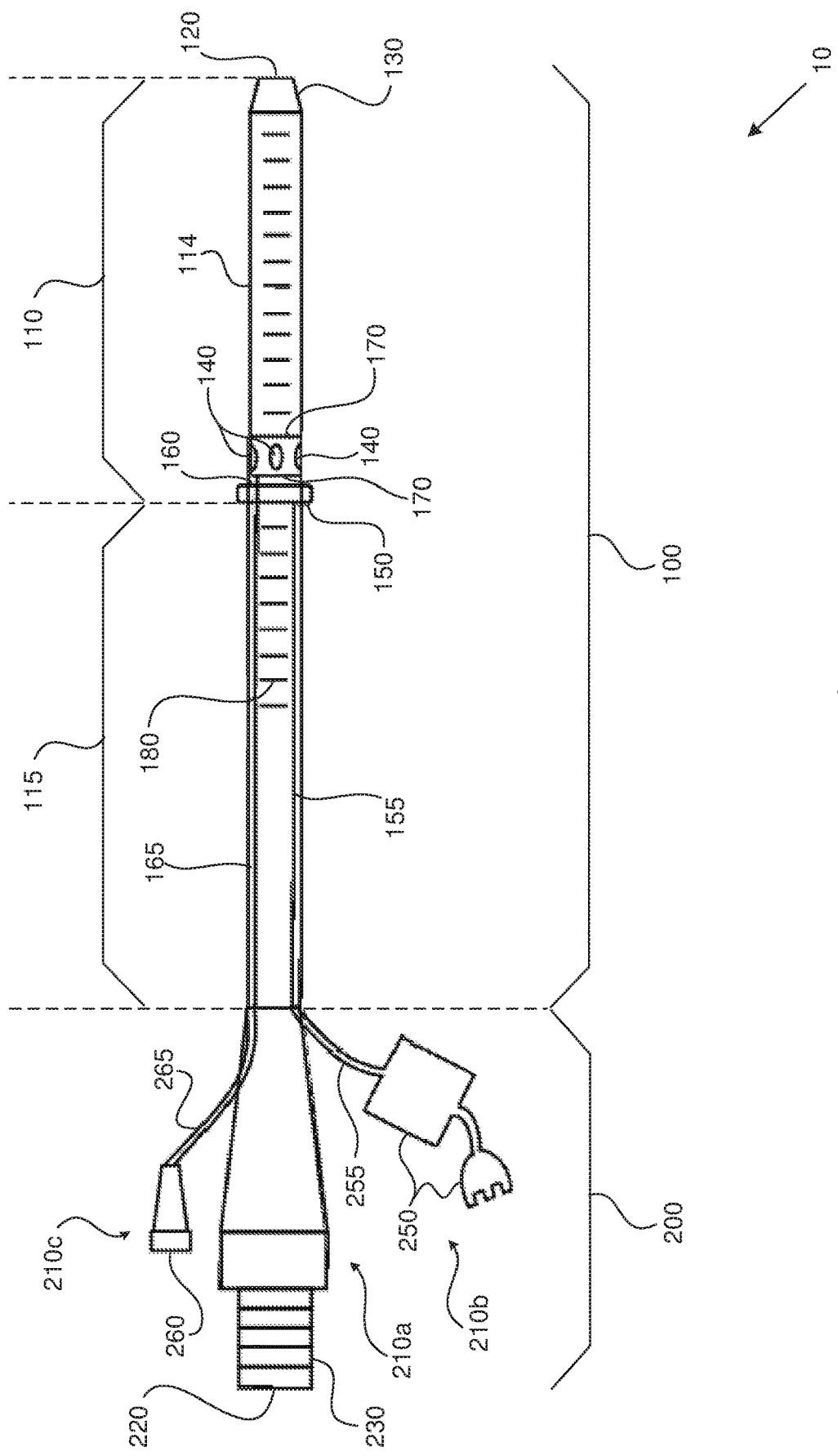
FIG. 1 is a schematic illustration of a first tube or cannula having multiple fenestrations in accordance with an embodiment of the present disclosure.

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in a FIG. or associated text is understood to mean "and/or" unless otherwise indicated. The recitation of a particular numerical value or value range herein is understood to include or be a recitation of an approximate numerical value or value range (e.g., within +/−5% to 10%).

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Math-*

*ematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, an object, a process, a physical parameter, or a value depending upon the type of set under consideration.

As used herein, the term "vessel" is taken to mean an anatomical vessel, passage, channel (e.g., a blood vessel, such as an artery) of a patient or subject, or an anatomical chamber or compartment. As used herein, the term "perfusion" is taken to mean the injection, transfer, or fluid communication of blood and/or one or more other fluids into a blood vessel for purpose of enabling the blood and/or other fluid(s) to reach an organ or tissues (e.g., to supply nutrients and oxygen). The term "fluidically coupled" is taken to mean coupled in a manner that provides for fluid (e.g., liquid or gas) communication. The term "antiparallel" is taken to mean parallel vectors that reside or lie along a common line, but which point in opposite directions.

Embodiments in accordance with the present disclosure are directed to a cannula or cannula structure (e.g., an arterial cannula) providing (a) a set of openings at a distal cannula portion, segment, end, or tip that is configured for entry into a vessel (e.g., an artery) at a cannulation site or point, and which is configured for displacement or travel along the vessel and positioning away from the cannulation point; and (b) a set of fenestrations, apertures, or openings configured to be positioned or maintained in position essentially or substantially immediately beyond the cannulation point. The set of fenestrations, in association with the set of openings at the cannula's distal tip, enable simultaneous perfusion of blood (and/or another fluid) into the cannulated vessel along multiple directions, including, opposing or anti-parallel flow directions relative to a central axis of the cannulated vessel, such that such blood introduced into the vessel by the cannula simultaneously flows towards the heart and away from the heart.

FIGS. 1-4 are schematic illustrations showing portions of a cannula assembly, cannula structure, or cannula (e.g., an arterial cannula) in accordance with an embodiment of the present disclosure. As indicated in FIG. 1, in an embodiment the cannula includes at least a first tube, tubular member, or tubular structure 10 providing a lumen therethrough and having an elongate first portion 100 coupled to a second portion 200, where the first portion 100 is distal to the second portion 200. The first portion 100 spans, extends along, or defines an elongate first fraction of the length of the first tube 10; and the second portion 200 spans, extends along, or defines a second fraction of the first tube's length. The first and second portions 100, 200 of the first tube 10 are coupled, joined, or formed together to enable fluid flow from a proximal opening 220 disposed at a proximal end 230 of the fist tube 10 toward, to, and through a set of distal openings 120 disposed at, along, or adjacent to a distal portion, segment, end, or tip 130 of the first tube 10. One having ordinary skill in the art will understand that the first tube 10 can itself be defined as the cannula, and hence the first tube's proximal opening 220 can be identified or defined as the cannula's proximal opening 220, and the first tube's distal opening(s) 120 can be defined as the cannula's distal opening(s) 120.

The first portion 100 of the first tube 10 includes a first or distal segment 110 that spans or extends along a first section of the first tube's elongate length, and which has a lumen therethrough which forms a portion of the first tube's lumen. The first segment 110 is coupled (e.g., integrally and fluidically coupled) to a second or proximal segment 115 of the first portion 100, which spans or extends along a second section of the first tube's elongate length, and which has a lumen therethrough (that is contiguous or aligned with the first segment's lumen). The first segment 110 is configured for entering into a vessel (e.g., an artery) at a cannulation site or point, and being positioned or displaced along or within the vessel such that the distal tip 130 of the first tube 10 resides at an intended or predetermined distance away from the cannulation point, at which blood and/or another fluid is intended to be perfused or directed into the cannulated vessel along a first direction through the first tube's distal opening(s) 120.

The first segment 110 carries a set of fenestrations 140 and a selectively expandable/inflatable cuff 150, which is typically flanged. In various embodiments, the first segment 110 includes an elongate projecting portion 114 between the first tube's distal opening(s) 120 and the set of fenestrations 140. The fenestrations 140 and the first tube's distal opening(s) 120 are configured for fluid communication with the first tube's proximal opening 220 and the second portion 200 by way of the first tube's first and second segments 110, 115. Blood and/or another fluid supplied to the first tube's proximal opening 220 flows towards the fenestrations 140 as well as the first tube's distal opening(s) 120. As further detailed below, the fenestrations 140 provide fluid entry sites, portals, or points other than the first tube's distal opening(s) 120 by which such blood and/or another fluid can enter into the cannulated vessel from the first segment 110 (or stated equivalently, the fenestrations 140 provide fluid output or discharge or release sites by which blood/fluid can be output or released or discharged from the first segment 110 into the cannulated vessel), and flow in a direction away from or opposite to a blood flow direction out of and beyond the first tube's distal opening(s) 120. Hence, the fenestrations 140 provide access sites through which blood and/or another fluid supplied to the first tube's proximal opening 220 can flow into the cannulated vessel along a second direction opposite or counter to the aforementioned first direction that is associated with the first tube's distal opening(s) 120.

For instance, in association with a VA ECMO procedure that employs a first tube 10 in accordance with an embodiment of the present disclosure which is inserted into an artery (e.g., the right femoral artery) of a body extremity (e.g., the right leg, correspondingly), blood supplied to the first tube's proximal opening 210 can flow through the first tube 10 and simultaneously flow (a) out of the first tube's distal opening(s) 120 into the body (e.g., directed up the aorta towards the heart); and (b) out of the first tube's fenestrations 140, away from the body and into the cannulated extremity. Thus, blood leaving the first tube's distal opening(s) 120 flows along a first direction (e.g., towards the heart), and blood leaving at least some of the first tube's fenestrations 140 flows along a second direction counter or opposite to the first direction (e.g., away from the heart). As a result, the risk of ischemia in the extremity is substantially or greatly reduced, or essentially eliminated.

Each of the fenestrations 140 can be configured or adapted to provide an intended shape, size, or fluid communication area (and not all fenestrations 140 need to have an identical shape, size, or fluid communication area). The fenestrations 140 are circumferentially or otherwise disposed about the first portion 110, slightly or very slightly distal or distally adjacent to the flanged cuff 150. In some embodiments, a boundary or dividing line between the first segment 110 and the second segment 115 can be defined at a proximal edge or border of the flanged cuff 150. The flanged cuff 150 is configured to facilitate clinician positioning or disposition of the fenestrations 140 at an intended position within the cannulated vessel, as further detailed below.

When the cannula is in use (i.e., when the vessel is cannulated/when the first tube 10 has been inserted into a patient or subject such that blood and/or another fluid can flow or is flowing from the first tube's proximal opening 220 toward its distal opening(s) 120 and out of the fenestrations 140 and the distal opening(s) 120), the first segment 110 is configured to reside entirely within the vessel. The second segment 115 and the second portion 200 are configured to almost or essentially entirely reside external to the vessel, outside of the patient's body. For instance, when the cannula is in use, only that portion of second segment 115 that is proximal to the expandable/inflatable cuff 150 and which is distal to the inner surface of the cannulated vessel's superficial wall resides within the vessel. The first segment 100 is flexible or pliable, and the second segment 200 is at least generally or somewhat flexible or pliable.

Figure 2:
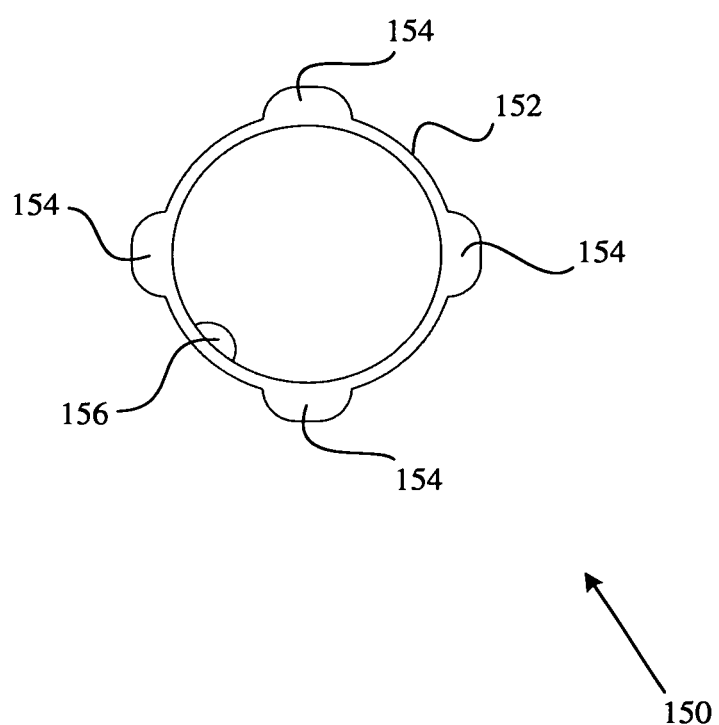
FIG. 2 is a schematic illustration of a front view of an expandable/inflatable flanged cuff in accordance with an embodiment of the present disclosure.

FIG. 2 is a schematic illustration of a front view of an expandable/inflatable flanged cuff 150 in accordance with an embodiment of the present disclosure. In various embodiments, the expandable or inflatable cuff 150 is configured to provide a cross sectional area that is larger than a cross sectional area of the first segment 110 at a location around the first segment at which the expandable or inflatable cuff is disposed. In an embodiment, the flanged cuff 150 includes an elliptical or circular ring or sleeve 152 that is shaped and dimensioned to surround an external, outer, or exterior diameter of the first tube's first segment 110, as indicated in FIG. 1 and as further indicated in FIG. 3A. The flanged cuff 150 carries a set of expandable/inflatable flange elements or members 154 (e.g., a plurality of flange members 154) peripherally (e.g., circumferentially) disposed about the sleeve 152. Each flange member 154 is coupled to an activation element/structure 156 corresponding to or carried by the cuff 150, which facilitates or enables selective outward expansion of the flange members 154 away (e.g., radially outward) from the sleeve 152, and hence away from the interior or lumen of the first segment 110; or inward contraction of the flange members 154 toward the sleeve 152, and hence toward the interior or lumen of the first segment 110. For instance, the activation element 156 can include or be an activation port 155 carried by the cuff 150, which is configured to facilitate or enable the communication of a fluid (e.g., air or a liquid) into or out of the flange members 154 to thereby inflate/expand or deflate/shrink the flange members 154, respectively. In some embodiments, flange members 154 can be carried by or form portions of a single shaped expandable structure. The activation element 156 when activated via the activation port 155 facilitates or enables the communication of the fluid (e.g., air or a liquid) into the single shaped expandable structure to thereby inflate/expand or deflate/collapse the plurality of flange members 154.

When the cannula is in use, at least a portion of the flanged cuff 150 is intended to reside adjacent to or in contact with the superficial wall of the cannulated vessel. After the first tube's first segment 110 has been inserted into a vessel through an appropriate entry point, the flanged cuff 150 can be expanded/inflated. Following such expansion or inflation, partial or slight withdrawal of the first tube 10 from the vessel causes portions of the flanged cuff 150 to contact the vessel's superficial wall, which imparts a resistive force that impedes the partial withdrawal of the first tube 10, and which identifies to a clinician a position at which the fenestrations 140 are disposed near, very near, or just beyond the cannulation point, slightly or very slightly past the superficial vessel wall. More particularly, the clinician will partially withdraw the first tube 10 slightly and gently until a resistive force that impedes the partial withdrawal of the first tube 10 is felt. Subsequent anchoring of the first tube's second segment 115 to the patient's skin secures the first tube 10 in an intended or correct position. In various embodiments, the flanged cuff 150 is configured for allowing blood flow around unflanged portions thereof. The sleeve 152 prevents total blockage of blood flow distally. Should the first tube 10 be advanced inadvertently, blood continues to flow distally between the deployed set of flange members. The flanged cuff 150 or a flange member 154 can include or be, for instance, an inflatable balloon or wire mesh structure.

Referring again to FIG. 1, radio-opaque markers 170 can be positioned proximal and/or distal to the set of fenestrations 140 to facilitate cannula positioning under fluoroscopic guidance. However, one having ordinary skill in the relevant art will understand that the cannula 10 can be positioned without fluoroscopic guidance. The cannula 10 can further include at least one graduated scale disposed on the exterior of the first tube 10 along portions of the first tube's elongate length, where the graduated scale includes graduated markings or indices 180 that can indicate a depth to which the cannula 10 has been positioned or placed within the cannulated vessel.

The second portion 200 of the first tube 10 proximally extends away from the first tube's second segment 115 toward and to the first tube's proximal opening 220. A proximal section 230 of the second portion 200 can provide or be a standard physical interface, coupling, or connection configured for mating engagement with and receiving blood and/or another fluid from a structure or device (e.g., a portion of a VA ECMO system) that is separate or separable from the first tube 10.

The first tube's second portion 200 is coupled to or includes a hub assembly 210, which in various embodiments includes a main hub 210a, a first auxiliary hub structure 210b, and a second auxiliary hub structure 210c. The main hub 210a proximally extends away from the second segment 115 of the first tube's first portion 100. In several embodiments, the first auxiliary hub structure 210b includes a flange member activation control interface/port 250 that is fluidically coupled to the flanged cuff's activation element or port 156. More particularly, the flange member control interface 250 can be fluidically coupled to the flanged cuff's activation port 156 by way of a first passage or channel 155 and a second passage or channel 255. The first passage 155 is carried by the first tube's second segment 115, for instance, along a portion of an interior or inner surface of the second segment 115. In some embodiments, the first tube's second segment 115 can be inserted further into and within the walls of the first tube 10. The second passage 255 provides a fluid communication pathway between the first passage 155 and the flange member control interface 250, and can extend away the first tube 10 (e.g., at, near, or generally near an interface between the first tube's first and second portions 100, 200) to the flange member control interface 250.

Figure 3A:
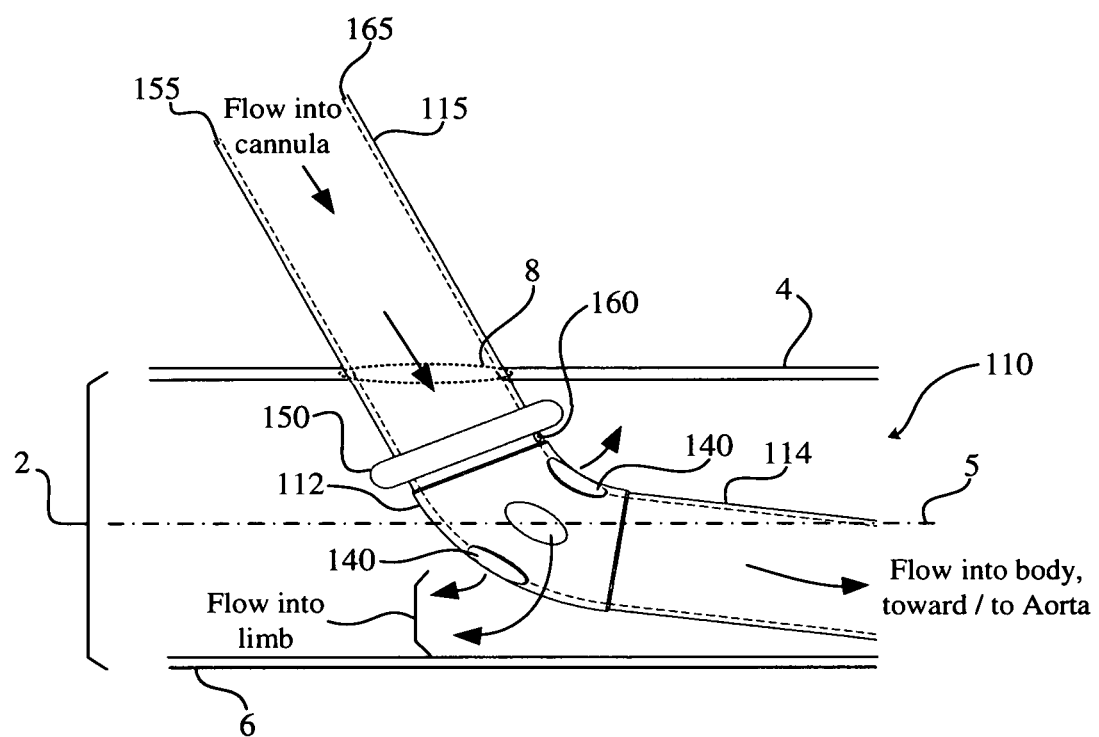
FIG. 3A is a representative illustration showing portions of first and second segments of the first tube positioned relative to a vessel entry site by which the first segment of the first tube has been positioned within a vessel.

FIG. 3A is a representative illustration showing portions of the first tube's first and second segments 110, 115 positioned relative to a vessel entry site or point 8 by which the first segment 110 of the first tube 10 has been positioned within a vessel 2. The vessel includes a superficial wall 4 and a deep vessel wall 6, in a manner readily understood by one having ordinary skill in the relevant art. A central axis 5 (e.g., a curvilinear axis) can be defined within the vessel 2, which passes through a center point or centroid of the vessel's cross sectional area.

As indicated in FIG. 3A, in various embodiments the fenestrations 140 are disposed on a flexible or semi-flexible angulatable section, element, member, or material 112 that is connected to or formed within the first segment 110. Once the fenestrations 140 have entered into the vessel 2, a portion of the first segment 110 distally adjacent or very near to the flanged cuff 150 can resemble a curve or an elbow by way of bending provided by the angulatable section 112. The angulatable section 112 can establish an intended or predetermined angular orientation or angle between the first portion's first and second segments 110, 115, for instance, approximately 45 degrees. Notwithstanding, the angulatable section's range of angulation can be from 0 to 180 degrees, or a fraction thereof. The flanged cuff 150 is disposed on the first segment 110, slightly proximal to the angulatable section 112. The majority of the length of the first segment 110 extends into the vessel 2, such that the first tube's distal opening(s) reside at an intended or predetermined vascular location or target site. In some embodiments, the angulatable section 112 can be structurally reinforced to enhance structural reliability, for instance, by way of one or more of material composition selection, material thickness selection, and/or the incorporation of one or more types of fibrous strands or materials (e.g., biocompatible natural or synthetic bendable fibres such as carbon fibres, optical fibres, or silk fibers), which can be oriented along predetermined directions, such as lengthwise/cross-wise/spiral-wise, relative to the elongate length of the first tube's first segment 110) in and/or through one or more portions of the angulatable section 112.

Referring again to FIG. 1 in association with FIG. 3A, the second auxiliary hub structure 210*c* can include a blood and/or fluid indicator interface 260, which is fluidicially coupled to a blood/fluid indicator port 160 carried by or formed within an interior or inner surface of the first segment 110. Such fluidic coupling of the blood/fluid indicator interface 260 to the blood/fluid indicator port 160 can be provided by way of a third passage or channel 165 and a fourth passage or channel 265, in a manner analogous or generally analogous to that described above in relation to the first passage 155 and the second passage 255, as will be readily understood by one having ordinary skill in the relevant art. In various embodiments, the fourth passage 265 is transparent or translucent, such that the presence of blood therein can be readily visually observed. The fluid indicator interface 260 and the fourth passage 265 can thus provide a visual indication to a clinician of whether the flanged cuff 150 and the fenestrations 140 have entered the vessel 2.

Once the fenestrations 140 and the flanged cuff 150 have entered the vessel 2 (e.g., as indicated by the blood/fluid indicator interface 260), the flanged cuff 150 can be expanded or inflated incrementally by the clinician or a machine interfacing with an indicating dial or meter to provide feedback with respect to an amount of air pressure infused into the flanged cuff 150, such that the flanged cuff 150 expands to have a cross sectional area or diameter that is larger than the entry site 8. The first tube 10 can then be partially or slightly withdrawn or displaced out of the entry site 8, causing at least some flange members 154 to contact or abut the inner surface of vessel's superficial wall 4. During partial withdrawal of the first tube 10, such contact of one or more flange members 154 with the superficial wall 4 provides perceptible tactile feedback to a clinician performing the cannulation, such that the clinician knows that the fenestrations 140 are correctly positioned within the vessel 2. The first tube 10 can then be anchored to the patient's skin, thereby rendering the first tube 10 substantially or essentially immobile relative to the vessel 2, in a manner readily understood by one having ordinary skill in the relevant art.

When the first tube 10 is in a correct position (and anchored such as described above), blood flowing through the second segment 115 of the first tube 10 toward and into the first tube's first segment 110 flows into the vessel 2 and exits the first segment 110 by way of (a) the first tube's distal opening(s) 120, and (b) the fenestrations 140. That is, a portion of the blood flowing into the first segment 110 exits the first segment 110 by way of the first tube's distal opening(s) 120, while a portion of the blood flowing into the first segment 110 concurrently exits the first segment 110 by way of the fenestrations 140.

At least some fenestrations 140 have cross sectional areas transverse to the vessel's central axis 5, which output, release, or discharge blood/fluid such that vector flow components of blood/fluid output by the fenestrations 140 along the central axis 5 are in opposition to vector flow components of blood/fluid output by the first tube's distal opening(s) 120 along the central axis 5. More particularly, blood exiting or output/released/discharged at the first tube's distal opening(s) 120 has a vector flow component that is tangential/parallel or generally tangential/parallel to the vessel's central axis 5, corresponding to a first flow direction. Blood exiting or output/released/discharged at least some of the fenestrations 140 has a vector flow component that is tangential/parallel or generally tangential/parallel to the vessel's central axis 5, corresponding to a second flow direction that is at least generally or approximately counter or opposite to (and which can be antiparallel to) the first flow direction.

Figure 3B:
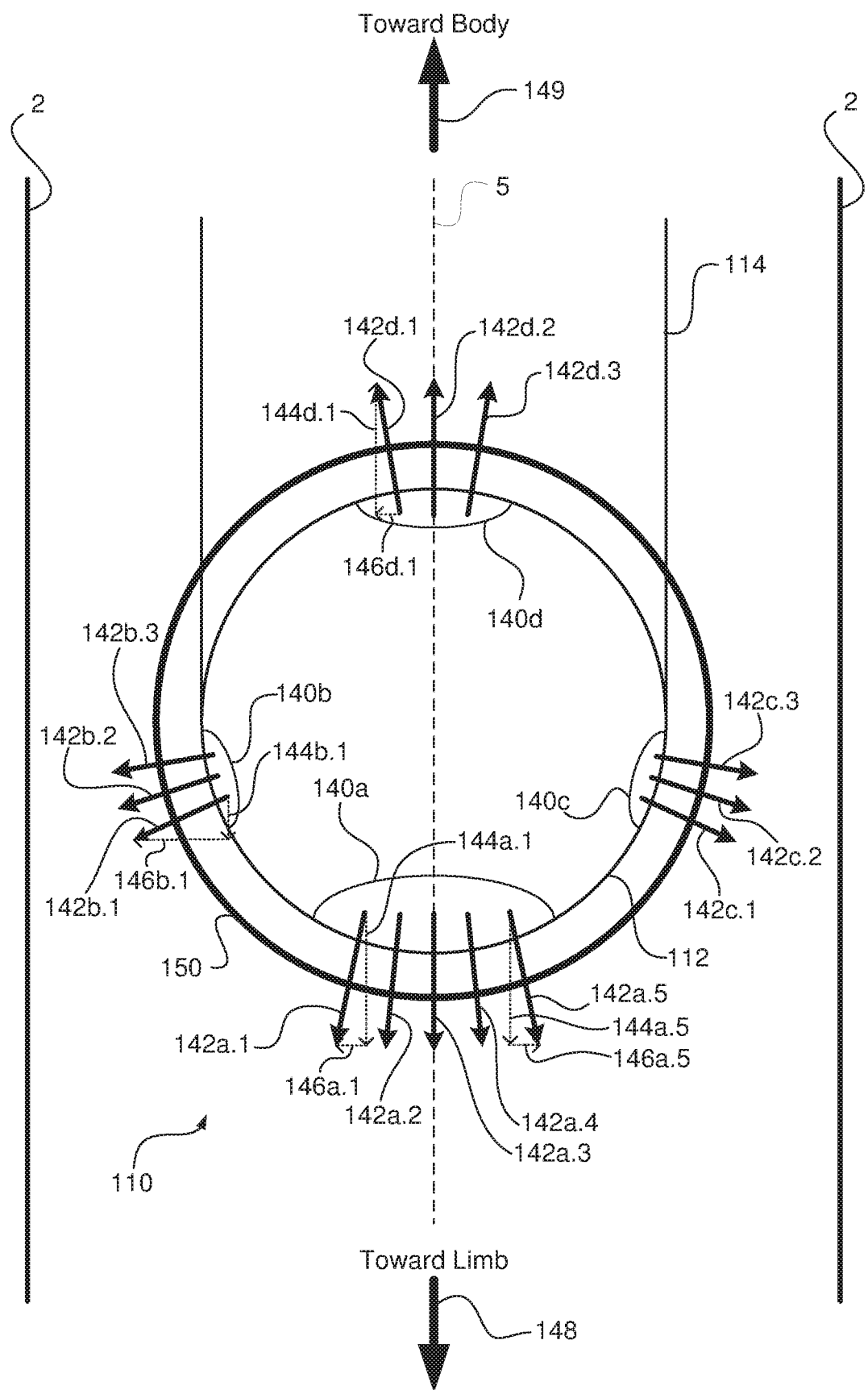
FIG. 3B is a representative top cross sectional illustration at or through an angulatable section in or on which a set of fenestrations resides, illustrating representative blood/fluid flow directions out of the set of fenestrations and into a cannulated vessel.

FIG. 3B is a representative top cross sectional illustration at or through an angulatable section 112 in or on which a set of fenestrations 140*a-d* resides, illustrating representative blood/fluid flow vectors 142 corresponding to the directional flow of blood/fluid through the set of fenestrations 140*a-d* into a cannulated vessel 2. As indicated in FIG. 3B, blood/fluid can be output, discharged, or released from each fenestration 140*a-d* into the vessel 2 in which the first tube's first segment 110 resides. In this representative non-limiting example provided to aid understanding, a first fenestration 140*a* outputs blood/fluid along flow vectors 142*a*.1-142*a*.5 that are generally or substantially aligned parallel to the vessel's central axis 5, such that blood/fluid output by the first fenestration 140*a* is primarily or substantially discharged along a first flow direction 148, e.g., toward/into a limb. Second and third fenestrations 140*b-c* output blood/fluid along flow vectors 142*b*.1-142*b*.3, 142*c*.1-142*c*.3 that are generally or substantially oriented toward the vessel's lateral walls; and a fourth fenestration 140*d* outputs blood/fluid along flow vectors 142*d*.1-142*d*.3 that are generally or substantially aligned parallel to the vessel's central axis 5, such that blood/fluid output by the fourth fenestration 140*d* is primarily or substantially discharged along a second flow direction 149, e.g., toward/into the body, which is counter or opposite to the first flow direction 148. One having ordinary skill in the relevant art will understand that with respect to FIG. 3B, blood/fluid additionally travels through and along the first segment's projecting portion 114, such that blood/fluid is additionally or simultaneously output by the first tube's distal opening(s) 120 into the vessel 2 generally or substantially along the second flow direction 149.

Any given flow vector 142 can be mapped to or represented as a parallel vector flow component 144 aligned parallel to the vessel's central axis 5, and a perpendicular vector flow component 146 aligned perpendicular to the vessel's central axis 5, in a manner readily understood by one having ordinary skill in the relevant art. At least some fenestrations 140a-c (e.g., at least one fenestration 140a, and in various embodiments, multiple fenestrations 140a-c) output blood/fluid into the vessel 2 such that flow vectors 142a-c corresponding to blood/fluid discharged thereby have parallel vector flow components 144a-c (e.g., parallel vector flow components 144a.1, 144a.5, 144b.1, etc. . . . ) that are oriented along the first flow direction, e.g., toward the limb. Additionally, in some embodiments, particular fenestrations 140d output blood/fluid into the vessel 2 such that flow vectors 142d corresponding to the blood/fluid discharged thereby have parallel vector flow components 144d (e.g., parallel vector flow component 144d.1, etc. . . . ) that are oriented along the second flow direction, e.g., toward the body, i.e., opposite or antiparallel to the parallel vector flow components 144a-c oriented toward the limb. Considered collectively, the set of fenestrations 140 provides a net blood/fluid flow that is directed toward the limb, counter or opposite to blood/fluid flow directed toward the body by the first tube's distal opening(s) 120 and possibly one or more fenestrations 140d.

As will be understood by one having ordinary skill in the relevant art, the number of fenestrations 140, the positions of the fenestrations 140 on the angulatable section 112, as well as the shapes and/or cross sectional areas of one or more fenestrations 140 can be selected relative to the shapes and/or cross sectional area(s) of one or more of the first tube's distal openings 120 in order to provide an intended or expected adequate/appropriate volume and/or rate of blood/fluid flow out of the first tube's distal opening(s) 120 relative to volume and/or rate of blood/fluid flow out of the fenestrations 140. In several representative embodiments, a ratio of a total fenestration area through which blood/fluid can exit the fenestrations 140 (e.g., a total cross sectional area for blood/fluid flow provided by the fenestrations 140) to a total distal opening area through which blood/fluid can exit the first tube's distal opening(s) 120 is not less than 10% and typically between 10%-40% (e.g., 20%-40%, 25%-35%, or 30%).

One having ordinary skill in the relevant art will further recognize that cannula assemblies, structures, and portions thereof in accordance with embodiments of the present disclosure can exhibit dimensions which are appropriate for the type of patient or subject (e.g., an infant or child versus a full grown adult) and/or the nature of a clinical situation under consideration. Depending upon embodiment or situational details, the first tube 10 can typically (but not exclusively) have an outer diameter of 3 mm (e.g., for infants) up to 15 mm (for adults).

FIG. 4 is a schematic illustration of a second tube 20 provided by a cannula assembly or structure in accordance with an embodiment of the present disclosure. One having ordinary skill in the relevant art will understand that the second tube 20 corresponds to or is a dilator assembly or dilator 20. The second tube 20 has a diameter smaller than the first tube 10, and is engageable therewith. The second tube 20 includes a central guide wire channel 22 configured for engaging with or passing a guide wire (not shown), as well as a tapered distal end 24 having a diameter that occludes the distal opening(s) of the first tube 10. The distal end 24 includes a through hole or opening therein 26 configured for passage of the guide wire. The guide wire can be 0.014 inch or 0.018 inch or 0.035 inch in diameter. Thus, the second tube 20 facilitates or enables percutaneous insertion of the first tube 10 into the vessel 2. The second tube 20 supports and stiffens the first tube 10 as the first tube 10 is inserted into the vessel 2. The second tube 20 additionally includes a hub 28 that is insertable into a main hub 210c of the first tube's hub assembly, in a manner readily understood by one having ordinary skill in the relevant art.

In a representative example femoral artery cannulation procedure for VA ECMO, the first tube 10 and second tube 20, henceforth simply referred to as the cannula 10 and the dilator assembly 20, are inserted into the femoral artery 2 until the blood/fluid indicator port 160 carried by the first tube's first segment 110 is inside the femoral artery 2. At this point, blood flows into the third and fourth passages 165, 265 and out through the blood/fluid indicator interface 260, thereby visually indicating to a clinician that the blood/fluid indicator port 160 is inside the femoral artery 2.

The cannula 10 is advanced 1-2 cm further, and the flanged cuff 150 is inflated or activated. This further advancement of the cannula 10 into the vessel 2 ensures that the flanged cuff 150 is well away from the superficial vessel wall to avoid and prevent accidental damage to the vessel 2 while inflating the flanged cuff 150. The cannula 10 is then gently pulled back until resistance is felt, which indicates contact of the flanged cuff 150 with the superficial vessel wall 4 and thus correct positioning of the cannula 10. The cannula 10 is then anchored into position to the patient's skin. The dilator assembly 20 is then withdrawn and the proximal end of the cannula 10 is attached to a pump circuit. Thus, the distal opening 120 of the cannula provides systemic blood flow to the body, while the fenestrations 140 provide blood flow to the limb. The likelihood of limb ischemia is thereby greatly reduced or avoided in patients undergoing extended cardiopulmonary bypass procedures.

Aspects of particular embodiments of the present disclosure address at least one aspect, problem, limitation, and/or disadvantage associated with exiting cannula assemblies or structures. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, components, processes, or alternatives thereof, may be desirably combined into other different systems, components, processes, and/or applications. In addition, various modifications, alterations, and/or improvements may be made to various embodiments that are disclosed by a person of ordinary skill in the art within the scope of the present disclosure.

The invention claimed is:

1. A method of cannulating an anatomical vessel of a patient through a vessel entry point and introducing concurrent flows of oxygenated blood into the anatomical vessel in opposing flow directions during a veno-arterial extra-corporeal membrane oxygenation (VA ECMO) procedure or a cardiopulmonary bypass procedure, the method comprising:
   (a) providing a cannula structure formed as an elongate tubular structure and having a length, the cannula structure comprising:
      a proximal opening configured to reside outside of the patient's body and by which oxygenated blood is introducible into the cannula structure for delivery into the anatomical vessel during the VA ECMO procedure or cardiopulmonary bypass procedure;

a plurality of fluid outputs, each of the plurality of fluid outputs fluidically coupled along the length of the cannula structure to the proximal opening of the cannula structure, the plurality of fluid outputs comprising:
  a distal opening configured for outputting into the anatomical vessel a first portion of said oxygenated blood in a first flow direction; and
  a set of fenestrations that is distinct and spaced proximally away from the distal opening, the set of fenestrations configured for outputting into the vessel a second portion of said oxygenated blood in a second flow direction counter to the first flow direction, simultaneous with the distal opening outputting the first portion of said oxygenated blood in the first flow direction;

a first tube disposed distal to the cannula structure's proximal opening, the first tube having an elongate length along which a plurality of fluidically coupled lumens extend therethrough, the first tube comprising:
  a first segment configured to entirely reside within the anatomical vessel during the VA ECMO procedure or cardiopulmonary bypass procedure, the first segment comprising:
    a first lumen having a proximal fluid input fluidically coupled to the proximal opening of the cannula structure and which is configured for receiving said oxygenated blood during the VA ECMO procedure or cardiopulmonary bypass procedure;
    an elongate projecting portion through which the first lumen extends; and
    the cannula structure's plurality of fluid outputs, wherein the distal opening resides near or at a distal end of the first tube,
    wherein the elongate projecting portion extends between the distal opening and the set of fenestrations,
    wherein the set of fenestrations resides on a section of the first segment that is (a) proximal to the elongate projecting portion, (b) configured to remain angulated within the vessel during the VA ECMO procedure or cardiopulmonary bypass procedure, and (c) disposed substantially beneath the vessel entry point such that the set of fenestrations outputs the second portion of said oxygenated blood substantially beneath the vessel entry point during the VA ECMO procedure or cardiopulmonary bypass procedure;
  a second segment proximal to the first segment and having a portion configured to reside external to the vessel during the VA ECMO procedure or cardiopulmonary bypass procedure and another portion configured to reside internal to the vessel during the VA ECMO procedure or cardiopulmonary bypass procedure, wherein the second segment comprises a second lumen aligned with the first lumen of the first segment, wherein between the cannula structure's proximal opening and distal opening the second segment is fluidically coupled to each of the cannula structure's proximal opening, the proximal fluid input of the first segment, the first lumen of the first segment, and the cannula structure's plurality of fluid outputs, and wherein the second segment is configured for receiving said oxygenated blood from the cannula structure's proximal opening and delivering said oxygenated blood into the proximal fluid input of the first segment during the VA ECMO procedure or cardiopulmonary bypass procedure; and
  an expandable or inflatable cuff which prior to and after expansion or inflation is disposed distal to the second segment and around the first segment at a first segment location slightly proximal to the set of fenestrations, wherein the expandable or inflatable cuff when expanded or inflated has a cross sectional area that is larger than each of a cross sectional area of the vessel entry point and the first segment at the location around the first segment at which the expandable or inflatable cuff is disposed, and wherein the expandable or inflatable cuff comprises:
    a sleeve configured for expansion away from or contraction toward the first lumen; and
    an activation member coupled to the sleeve and configured for selectively expanding or contracting the sleeve,
    wherein the expandable or inflatable cuff when expanded or inflated is configured to reside entirely within the vessel in a position substantially beneath and immediate to the vessel entry point adjacent to the superficial wall of the vessel, proximal to the set of fenestrations relative to the length of the first tube when the vessel is cannulated and the first tube is in a correct position within the vessel during the VA ECMO procedure or cardiopulmonary bypass procedure;

(b) introducing the distal end of the first tube into the anatomical vessel through the vessel entry point;

(c) after (b), advancing portions of the first tube into the anatomical vessel until the first segment including the set of fenestrations resides within the anatomical vessel;

(d) after (c), further advancing the first tube into the anatomical vessel, such that the first segment including the set of fenestrations, the expandable or inflatable cuff, and a portion[s] of the second segment reside within the anatomical vessel;

(e) after (d), expanding or inflating the expandable or inflatable cuff;

(f) after (e), withdrawing portions of the cannula structure from the anatomical vessel until resistance is felt, indicating each of: the expandable or inflatable cuff has contacted the superficial wall of the anatomical vessel, at least a portion of the expandable or inflatable cuff resides adjacent to or in contact with the superficial wall of the anatomical vessel, and the first tube is in a correct position; and (g) after (f), while the first tube is in the correct position, anchoring portions of the cannula structure to the patient's skin, whereby only that portion of second segment that is proximal to the expandable or inflatable cuff and which is distal to the inner surface of the cannulated vessel's superficial wall resides within the vessel;

(h) after (g), supplying said oxygenated blood to the cannula structure's proximal opening; and (i) after (h), discharging the first portion of said oxygenated blood out of the distal opening in the first flow direction simultaneous with discharging the second portion of said oxygenated blood into the anatomical vessel out of the set of fenestrations in the second flow direction.

2. The method of claim 1, wherein a vector flow component along a central axis of the anatomical vessel corresponding to blood output by at least some fenestrations within the set of fenestrations is antiparallel to a vector flow component along the central axis of the anatomical vessel corresponding to blood output by the distal opening.

3. The method of claim 1, wherein the distal opening provides systemic blood flow to the patient's body, while the set of fenestrations provides blood flow to a limb of the patient's body during the VA ECMO or cardiopulmonary bypass procedure.

4. The method of claim 1, wherein supplying said oxygenated blood to the cannula structure's proximal opening comprises attaching the proximal end of the cannula structure to a pump circuit.

5. The method of claim 1, wherein the first segment carries a blood indicator port that is fluidically coupled to a blood indicator interface corresponding to a hub structure associated with the cannula structure, and wherein (c) of the method comprises: after (b), advancing the first tube into the anatomical vessel until the blood indicator interface indicates that the set of fenestrations resides within the anatomical vessel.

6. The method of claim 1, wherein the activation member is fluidically coupled to an activation port carried by the expandable or inflatable cuff, and wherein (e) of the method comprises: after (d), expanding or inflating the expandable or inflatable cuff by way of communication of a fluid into the activation port.

7. The method of claim 1, wherein the expandable or inflatable cuff is flanged.

8. The method of claim 7, wherein the expandable or inflatable cuff includes a plurality of flange members that can be outwardly expandable away from and inwardly contracted toward the lumen of the first segment on a selective basis.

9. A method of cannulating an anatomical vessel of a patient through a vessel entry point and introducing concurrent flows of oxygenated blood into the anatomical vessel in opposing flow directions during a veno-arterial extra-corporeal membrane oxygenation (VA ECMO) procedure or a cardiopulmonary bypass procedure, the method comprising:
(a) providing a cannula structure formed as an elongate tubular structure and having a length, the cannula structure comprising:
a proximal opening configured to reside outside of the patient's body and by which oxygenated blood is introducible into the cannula structure for delivery into the anatomical vessel during the VA ECMO procedure or cardiopulmonary bypass procedure;
a plurality of fluid outputs, each of the plurality of fluid outputs fluidically coupled along the length of the cannula structure to the proximal opening of the cannula structure, the plurality of fluid outputs comprising:
a distal opening configured for outputting into the anatomical vessel a first portion of said oxygenated blood in a first flow direction; and
a set of fenestrations that is distinct and spaced proximally away from the distal opening, the set of fenestrations configured for outputting into the vessel a second portion of said oxygenated blood in a second flow direction counter to the first flow direction, simultaneous with the distal opening outputting the first portion of said oxygenated blood in the first flow direction;
a first tube disposed distal to the cannula structure's proximal opening, the first tube having an elongate length along which a plurality of fluidically coupled lumens extend therethrough, the first tube comprising:
a first segment configured to entirely reside within the anatomical vessel during the VA ECMO procedure or cardiopulmonary bypass procedure, the first segment comprising:
a first lumen having a proximal fluid input fluidically coupled to the proximal opening of the cannula structure and which is configured for receiving said oxygenated blood during the VA ECMO procedure or cardiopulmonary bypass procedure;
an elongate projecting portion through which the first lumen extends; and
the cannula structure's plurality of fluid outputs, wherein the distal opening resides near or at a distal end of the first tube,
wherein the elongate projecting portion extends between the distal opening and the set of fenestrations,
wherein the set of fenestrations resides on an angulatable section of the first segment that (a) has a range of angulation between 0 and 180 degrees, or a fraction thereof, (b) is proximal to the elongate projecting portion, and (c) is disposed substantially beneath the vessel entry point such that the set of fenestrations outputs the second portion of said oxygenated blood substantially beneath the vessel entry point during the VA ECMO procedure or cardiopulmonary bypass procedure;
a second segment proximal to the first segment and having a portion configured to reside external to the vessel during the VA ECMO procedure or cardiopulmonary bypass procedure and another portion configured to reside internal to the vessel during the VA ECMO procedure or cardiopulmonary bypass procedure, wherein the second segment comprises a second lumen aligned with the first lumen of the first segment, wherein between the cannula structure's proximal opening and distal opening the second segment is fluidically coupled to each of the cannula structure's proximal opening, the proximal fluid input of the first segment, the first lumen of the first segment, and the cannula structure's plurality of fluid outputs, and wherein the second segment is configured for receiving said oxygenated blood from the cannula structure's proximal opening and delivering said oxygenated blood into the proximal fluid input of the first segment during the VA ECMO procedure or cardiopulmonary bypass procedure,
wherein the angulatable section of the first segment is configured for establishing an intended or predetermined angular orientation between the first segment and the second segment during the VA ECMO procedure or cardiopulmonary bypass procedure; and
an expandable or inflatable cuff which prior to and after expansion or inflation is disposed distal to the second segment and around the first segment at a first segment location slightly proximal to the set of fenestrations, wherein the expandable or inflatable cuff when expanded or inflated has a cross sectional area that is larger than each of a cross sectional area of the vessel entry point and the first segment at the location around the first segment at which the expandable or inflatable cuff is disposed, and wherein the expandable or inflatable cuff comprises:

a sleeve configured for expansion away from or contraction toward the first lumen; and an activation member coupled to the sleeve and configured for selectively expanding or contracting the sleeve, wherein the expandable or inflatable cuff when expanded or inflated is configured to reside entirely within the vessel in a position substantially beneath and immediate to the vessel entry point adjacent to the superficial wall of the vessel, proximal to the set of fenestrations relative to the length of the first tube when the vessel is cannulated and the first tube is in a correct position within the vessel during the VA ECMO procedure or cardiopulmonary bypass procedure;

(b) introducing the distal end of the first tube into the anatomical vessel through the vessel entry point;

(c) after (b), advancing portions of the first tube into the anatomical vessel until the first segment including the set of fenestrations resides within the anatomical vessel;

(d) after (c), further advancing the first tube into the anatomical vessel, such that the first segment including the set of fenestrations, the expandable or inflatable cuff, and a portion[s] of the second segment reside within the anatomical vessel;

(e) after (d), expanding or inflating the expandable or inflatable cuff;

(f) after (e), withdrawing portions of the cannula structure from the anatomical vessel until resistance is felt, indicating each of: the expandable or inflatable cuff has contacted the superficial wall of the anatomical vessel, at least a portion of the expandable or inflatable cuff resides adjacent to or in contact with the superficial wall of the anatomical vessel, and the first tube is in a correct position; and (g) after (f), while the first tube is in the correct position, anchoring portions of the cannula structure to the patient's skin, whereby only that portion of second segment that is proximal to the expandable or inflatable cuff and which is distal to the inner surface of the cannulated vessel's superficial wall resides within the vessel;

(h) after (g), supplying said oxygenated blood to the cannula structure's proximal opening; and (i) after (h), discharging the first portion of said oxygenated blood out of the distal opening in the first flow direction simultaneous with discharging the second portion of said oxygenated blood into the anatomical vessel out of the set of fenestrations in the second flow direction.

* * * * *